US012778469B2

(12) United States Patent
Yang

(10) Patent No.: US 12,778,469 B2
(45) Date of Patent: Nov. 3, 2026

(54) INSTALLATION UNIT OF ANALYTE DETECTION DEVICE

(71) Applicant: MEDTRUM TECHNOLOGIES INC., Shanghai (CN)

(72) Inventor: Cuijun Yang, Shanghai (CN)

(73) Assignee: MEDTRUM TECHNOLOGIES INC., Shanghai (CN)

( * ) Notice: Subject to any disclaimer, the term of this patent is extended or adjusted under 35 U.S.C. 154(b) by 940 days.

(21) Appl. No.: 18/014,476

(22) PCT Filed: May 31, 2021

(86) PCT No.: PCT/CN2021/097158
§ 371 (c)(1),
(2) Date: Jan. 5, 2023

(87) PCT Pub. No.: WO2022/007537
PCT Pub. Date: Jan. 13, 2022

(65) Prior Publication Data
US 2023/0248278 A1 Aug. 10, 2023

(51) Int. Cl.
*A61B 5/1473* (2006.01)
*A61B 5/145* (2006.01)

(52) U.S. Cl.
CPC ........ *A61B 5/1473* (2013.01); *A61B 5/14532* (2013.01); *A61B 2560/063* (2013.01)

(58) Field of Classification Search
CPC .............. A61B 5/1473; A61B 5/14532; A61B 2560/063; A61B 5/6849; A61B 5/14503; A61B 5/6801
See application file for complete search history.

(56) References Cited

U.S. PATENT DOCUMENTS

2019/0342637 A1* 11/2019 Halac ........................ H04Q 9/00
2021/0290115 A1* 9/2021 Chae ................ A61B 5/150206

FOREIGN PATENT DOCUMENTS

CN 201492421 6/2010
CN 104887242 9/2015
CN 106137214 11/2016
(Continued)

OTHER PUBLICATIONS

"International Search Report (Form PCT/ISA/210) of PCT/CN2021/097158", mailed on Sep. 1, 2021, with English translation thereof, pp. 1-4.

*Primary Examiner* — Christian Jang
(74) *Attorney, Agent, or Firm* — JCIP GLOBAL INC.

(57) ABSTRACT

An installation unit of an analyte detection device, includes: a sensor unit, which is provided near a front end of the installation unit; a trigger component, prior to starting the trigger component, the installation unit not performing an installation action; an auxiliary needle module, which is used to prick the in vivo part of a sensor under the skin; a parallel slider module, which is used to carry the sensor unit; a base, which is embedded in the installation unit from the front end of the installation unit; an elastic assembly, which is sleeved on the auxiliary needle module; and an outer casing, which is used to carry the trigger component, the auxiliary needle module, the parallel slider module, and the base. The installation unit has a simple and compact structure, a small size, low production and fabrication costs, and is convenient for users to use.

19 Claims, 12 Drawing Sheets

(56) References Cited

FOREIGN PATENT DOCUMENTS

| | | |
|---|---|---|
| CN | 109998555 | 7/2019 |
| CN | 111384540 | 7/2020 |
| WO | 2018027940 | 2/2018 |

* cited by examiner

INSTALLATION UNIT OF ANALYTE DETECTION DEVICE

CROSS-REFERENCE TO RELATED APPLICATION

This application is a 371 of international application of PCT application serial no. PCT/CN2021/097158, filed on May 31, 2021, which claims the priority benefit of PCT application serial no. PCT/CN2020/100597, filed on Jul. 7, 2020. The entirety of each of the above-mentioned patent applications is hereby incorporated by reference herein and made a part of this specification.

TECHNICAL FIELD

The invention mainly relates to the field of medical devices, in particular to an installation unit of analyte detection device.

BACKGROUND

The pancreas in a normal human body can automatically monitor the blood glucose level and automatically secrete required amount of insulin/glucagon. In the body of a type 1 diabetes patient, the pancreas does not function properly and cannot produce enough insulin for the body. Therefore, type 1 diabetes is a metabolic disease caused by abnormal pancreatic function, and diabetes is a lifelong disease. At present, there is no cure for diabetes with medical technology. The onset and development of diabetes and its complications can only be controlled by stabilizing blood glucose.

Diabetics need to have their blood glucose measured before they inject insulin into the body. At present, most of the testing methods can continuously measure blood glucose level and transmit the data to a remote device in real time for the user to view. This method is called Continuous Glucose Monitoring (CGM).

The method requires the detection device to be stuck on the skin surface, and the sensor carried by the detection device is punctured into the subcutaneous tissue fluid to complete the detection. However, the size of the installation unit of the current detection devices on the market is generally too large, which makes it inconvenient for users to operate, and on the other hand, the installation unit is discarded after being used once, which makes the production cost too high.

Therefore, the prior art urgently needs an installation unit of analyte detection device with simple and compact structure, small size and easily use for users.

SUMMARY OF INVENTION

The embodiment of the invention discloses an installation unit of analyte detection device. Before installation, the sensor base is fixed on the outer shell of the installation unit to form a closed structure with the outer shell. The design of the shape, size and location of each structural member in the installation unit makes the installation unit have a smaller overall size. Users can complete the installation steps with one hand, which is convenient for users and reduces the production cost. At the same time, during and after the installation, it is not necessary to adjust the shape of the sensor to avoid the breakage of the electrode or electrode lead on the sensor surface and improve the reliability of the analyte detection device.

The invention provides an installation unit of analyte detection device, which comprises a sensor unit, the sensor unit comprising a sensor base and a sensor arranged on the sensor base, and the sensor comprising an external part and an internal part. The installation unit does not implement the installation action before starting the trigger component. The auxiliary-needle module comprises an auxiliary-needle, and the auxiliary-needle at least comprises an opening area which encloses the internal part and is suitable for feeding the internal part into the subcutaneous. A parallel slider module suitable for carrying the sensor unit. The base is embedded into the installation unit from the front end of the installation unit, and an installation area suitable for installing the sensor unit is arranged on the base. The outer shell is used for carrying the trigger component, the auxiliary-needle module, the parallel slider module and the base. The elastic component, which comprises the first elastic component and the second elastic component, is in a compressed state and is suitable for providing the elastic force required by the installation unit to implement the installation action.

According to one aspect of the invention, the external part is a plane structure.

According to one aspect of the invention, the external part is bent or bent towards the top of the sensor base, laid flat on the top of the sensor base, and the external part is in the working position.

According to one aspect of the invention, the external part and the internal part are vertical.

According to one aspect of the invention, the outer shell is provided with a first clamp part on the outer shell, the sensor unit is provided with a first clamp part of the sensor, and the first clamp part of the outer shell and the first clamp part of the sensor are mutually clamped.

According to one aspect of the invention, the trigger component comprises a trigger paddle, the outer shell comprises a through-hole arranged on the side wall, and the trigger paddle enters into the outer shell through the through-hole.

According to one aspect of the invention, when implementing the installation action, trigger paddle pushes the first clamp part of the outer shell to release the snap state of the first clamp part of the outer shell and the first clamp part of the sensor.

According to one aspect of the invention, the trigger component comprises a trigger button and an anti-trigger structure, the anti-trigger structure comprises a breakable structure and a break button, and the break button is suitable for preventing the trigger button from starting before the break of the breakable structure, thereby implementing the installation action.

According to one aspect of the invention, the trigger component comprises a reset elastic component, which is suitable for returning the trigger button to its initial position after starting.

According to one aspect of the invention, the trigger component also comprises a limit clip, the outer shell comprises a limit hole, and the limit clip and the limit hole form a snap connection to prevent the trigger button from separating from the outer shell when the trigger button returns to the initial position.

According to one aspect of the invention, the opening area is circular arc or "V" shape.

According to one aspect of the invention, the outer shell comprises a limit column, the auxiliary-needle module comprises a chute, the parallel slider module comprises a through-hole of the limit column, the chute and the through-hole of the limit column are respectively matched with the limit column, which is suitable for making the auxiliary-needle module and the parallel slider module slide in the outer shell.

According to one aspect of the invention, the first elastic component is located between the outer shell and the parallel slider module.

According to one aspect of the invention, the second elastic component is located between the auxiliary-needle module and the parallel slider module.

According to one aspect of the invention, the auxiliary-needle module is provided with a cylinder clamp part, the parallel slider module is provided with a parallel slider clamp part, the cylinder clamp part and the parallel slider clamp part are mutually clamped, which is suitable for making the auxiliary-needle module slide with the parallel slider module in the direction of the base, and when the auxiliary-needle module slides to a preset position, the cylinder clamp part and the parallel slider clamp part release the elasticity of the second elastic part, the auxiliary-needle module is pushed back to the initial position.

According to one aspect of the invention, the outer shell is provided with a third clamp part of the outer shell, the base is provided with a first clamp part of the base, and the third clamp part of the outer shell and the first clamp part of the base are mutually clamped, which is suitable for fixing the base on the outer shell.

According to one aspect of the invention, the third clamp part of the outer shell is provided with a limit bulge, and the parallel slider module is provided with a parallel slider bulge, which is suitable for making the parallel slider module slide toward the base direction. When the parallel slider module slides, the limit bulge and the parallel slider bulge cooperate to push the third clamp part of the outer shell apart, so as to release the snap state of the third clamp part of the outer shell and the first clamp part of the base, and release the base.

According to one aspect of the invention, the installation area of the base is provided with a second clamp part of the base, the sensor unit is provided with a second clamp part of the sensor, and the second clamp part of the base can form a snap connection with the second clamp part of the sensor.

According to one aspect of the invention, the base comprises adhesive tape, which is suitable for pasting the base on the surface of human skin.

Compared with the prior art, the technical scheme of the invention has the following advantages:

In the installation unit of the analyte detection device disclosed by the invention, the sensor unit, trigger component, auxiliary-needle module, parallel slider module, base, and elastic component are all arranged on or inside the outer shell, and the overall size of the installation unit can be greatly reduced through appropriate structural member shape design and spatial layout design, and the user can complete the installation step with one hand.

Further, the external part of the sensor is a planar structure, which is conducive to its electrical connection with the transmitter.

Further, the external part of the sensor bends or folds towards the top of the sensor base, and is laid flat on the top of the sensor base. The planar external part is laid flat on the top of the sensor base, reducing the overall height of the sensor unit, thereby reducing the thickness of the analyte detection device base. Since the base needs to be embedded in the installation unit before installation, the height of the installation unit is also reduced.

Further, the external part of the sensor is perpendicular to the internal part, which can optimize the design of the internal structure of the installation unit, simplify the user's operation steps when installing the sensor unit, and facilitate puncture.

Further, the sensor unit is clamped with the outer shell, while the sensor unit is placed on the parallel slider module, which indirectly realizes the clamping between the parallel slider module and the outer shell. It is unnecessary to repeatedly design the clamping structure between the parallel slider module and the outer shell, simplifying the structure of the outer shell and the parallel slider module, and reducing the manufacturing and processing costs.

Further, the trigger button located outside the outer shell can release the snap connection between the sensor unit and the outer shell through the trigger paddle extending inside the outer shell, which is simple in structure. At the same time, the space inside the outer shell is reasonably utilized, and the overall size of the outer shell is reduced.

Further, the installation unit of the analyte detection device also comprises an anti-trigger structure, which is matched with the trigger component. Before removal, the anti-trigger structure prevents the trigger component from starting. The anti-trigger structure can prevent the trigger components from being started wrongly before installation, thus preventing the auxiliary-needle from popping out and ensuring safe use.

Further, in order to avoid the failure to successfully start the installation action of the installation unit by pressing the trigger button, a reset elastic component is also designed in the trigger component, which can be pressed again after the trigger button returns to the initial position, so that multiple triggering actions can be achieved until the installation unit successfully starts the installation action.

Further, the limit clip on the trigger component can prevent the trigger button from leaving the outer shell when resetting, and ensure that the trigger button can be pressed for use for many times.

Further, the first elastic component and the second elastic component are respectively located between the outer shell and the parallel slider module, and between the auxiliary-needle module and the parallel slider module, making full use of the inner space of the outer shell between the structural members, compact in structure, and reducing the overall size of the outer shell.

Further, the parallel slider module drives the auxiliary-needle module to slide together through the clamping connection. The sliding of the parallel slider module can push the sensor unit into the installation area of the chassis, while the sliding of the auxiliary-needle module can send the part of the sensor body into the subcutaneous area. Both of them are carried out and completed simultaneously, which is convenient for users to operate. In addition, it does not need to use additional elastic parts to push the auxiliary-needle module to slide, reducing the number of structural parts, reduced manufacturing costs.

Further, the auxiliary-needle module can return to the initial position under the elastic force of the second elastic part after sending internal part into the subcutaneous, so as to prevent the auxiliary-needle from being exposed outside the outer shell, causing unnecessary safety accidents.

DESCRIPTION OF EMBODIMENTS

As mentioned above, the size of the installation unit of the analyte detection device in the prior art is generally too large, which makes it inconvenient for users to operate, and on the other hand, the installation unit can be discarded after being used once. The excessive size makes the production cost too high.

In order to solve the problem, the invention provides an installation unit of analyte detection device, which is simple and compact in structure, small in size, convenient for users to operate, and low in production and manufacturing cost.

Various exemplary embodiments of the invention will now be described in detail with reference to the attached drawings. It is understood that, unless otherwise specified, the relative arrangement of parts and steps, numerical expressions and values described in these embodiments shall not be construed as limitations on the scope of the invention.

In addition, it should be understood that the dimensions of the various components shown in the attached drawings are not necessarily drawn to actual proportions for ease of description, e.g. the thickness, width, length or distance of some elements may be enlarged relative to other structures.

The following descriptions of exemplary embodiments are illustrative only and do not in any sense limit the invention, its application or use. Techniques, methods and devices known to ordinary technicians in the relevant field may not be discussed in detail here, but to the extent applicable, they shall be considered as part of this manual.

It should be noted that similar labels and letters indicate similar items in the appending drawings below, so that once an item is defined or described in one of the appending drawings, there is no need to discuss it further in the subsequent appending drawings.

Figure 1A:
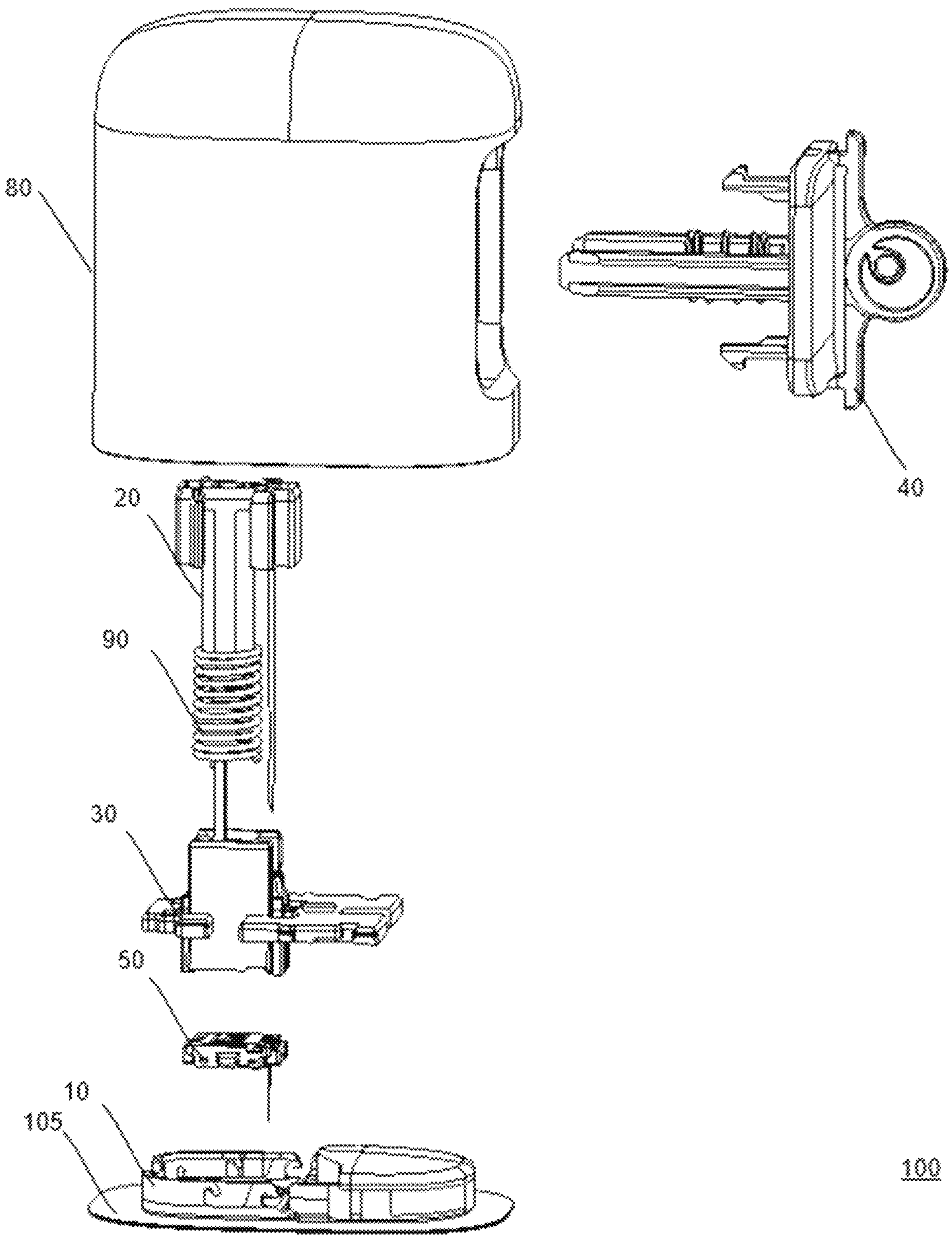
FIG. 1*a* is the structural explosion diagram of the installation unit according to an embodiment of the invention.
Figure 1B:
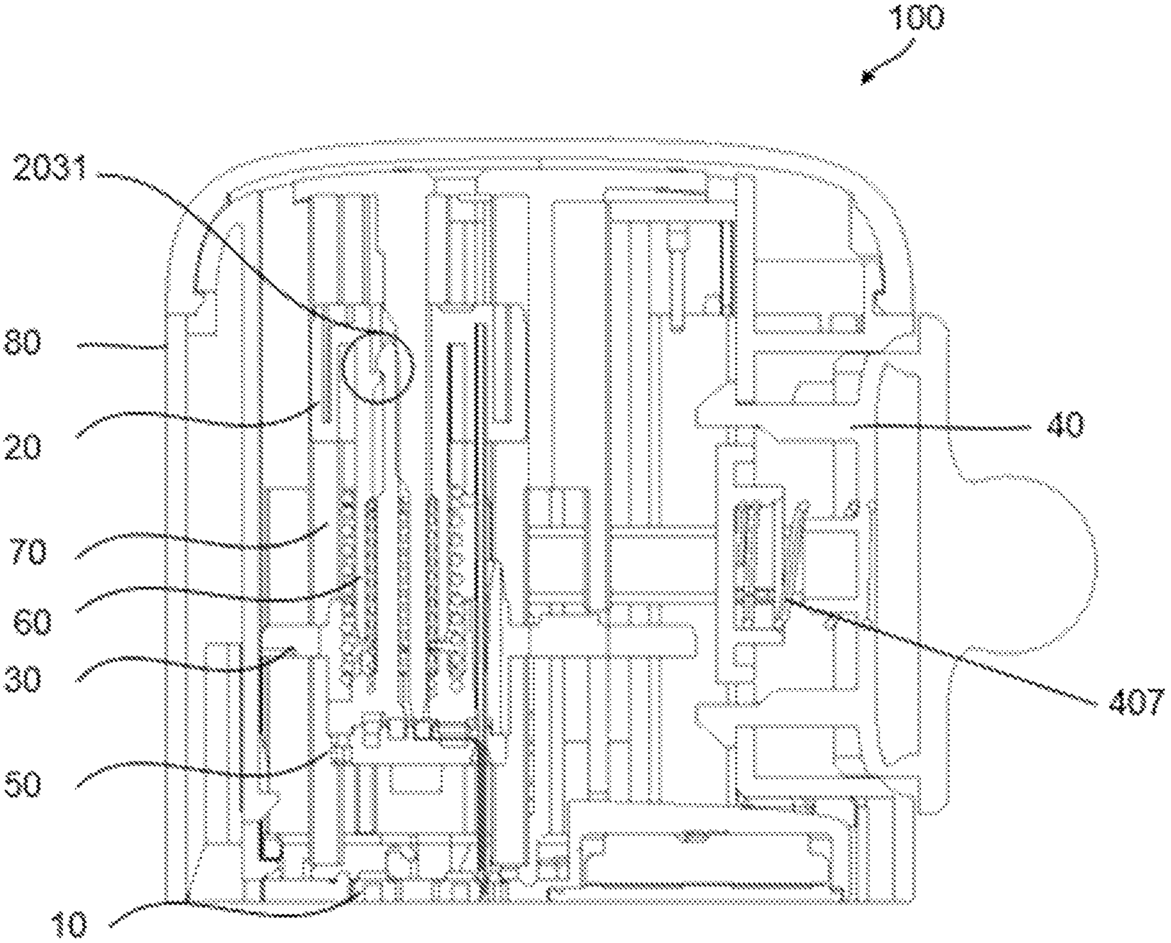
FIG. 1*b* is the sectional structure diagram of the installation unit according to an embodiment of the invention.
Figure 2A:
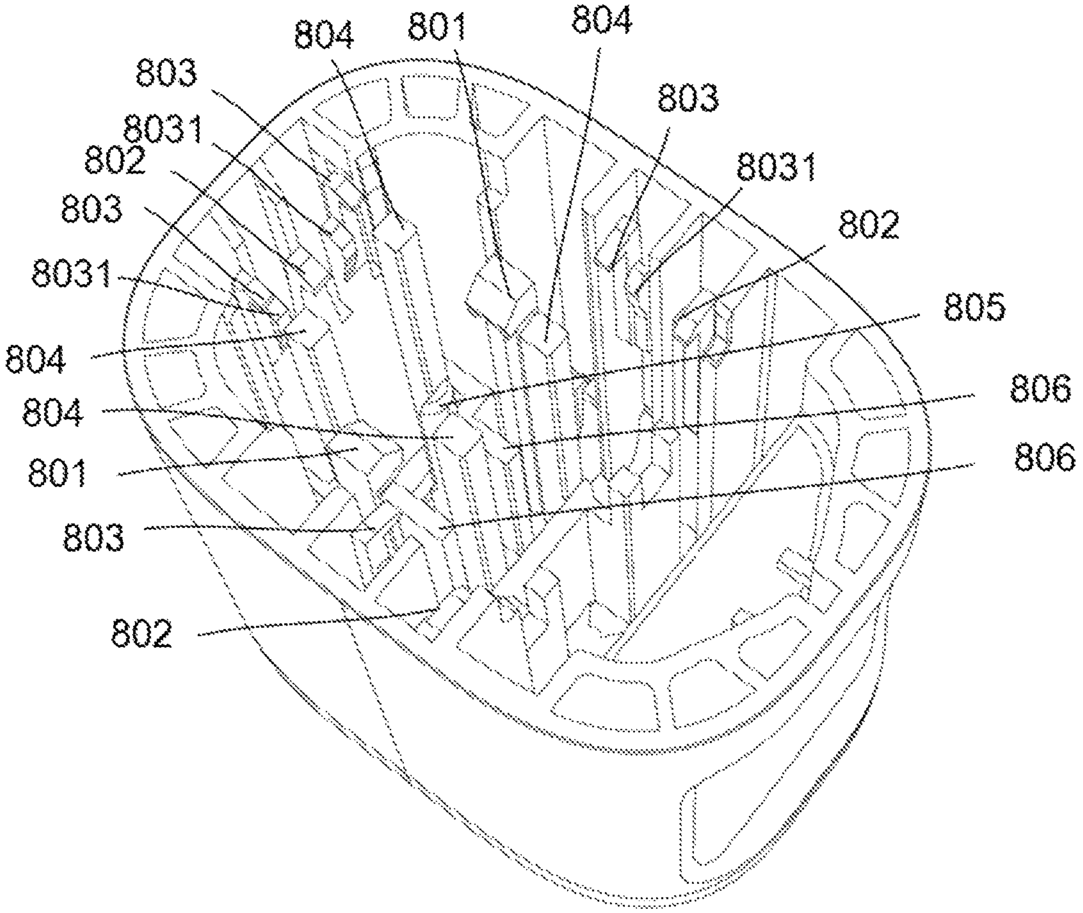
FIG. 2*a* is the schematic diagram of the three-dimensional structure of an exemplary outer shell according to the invention.
Figure 2B:
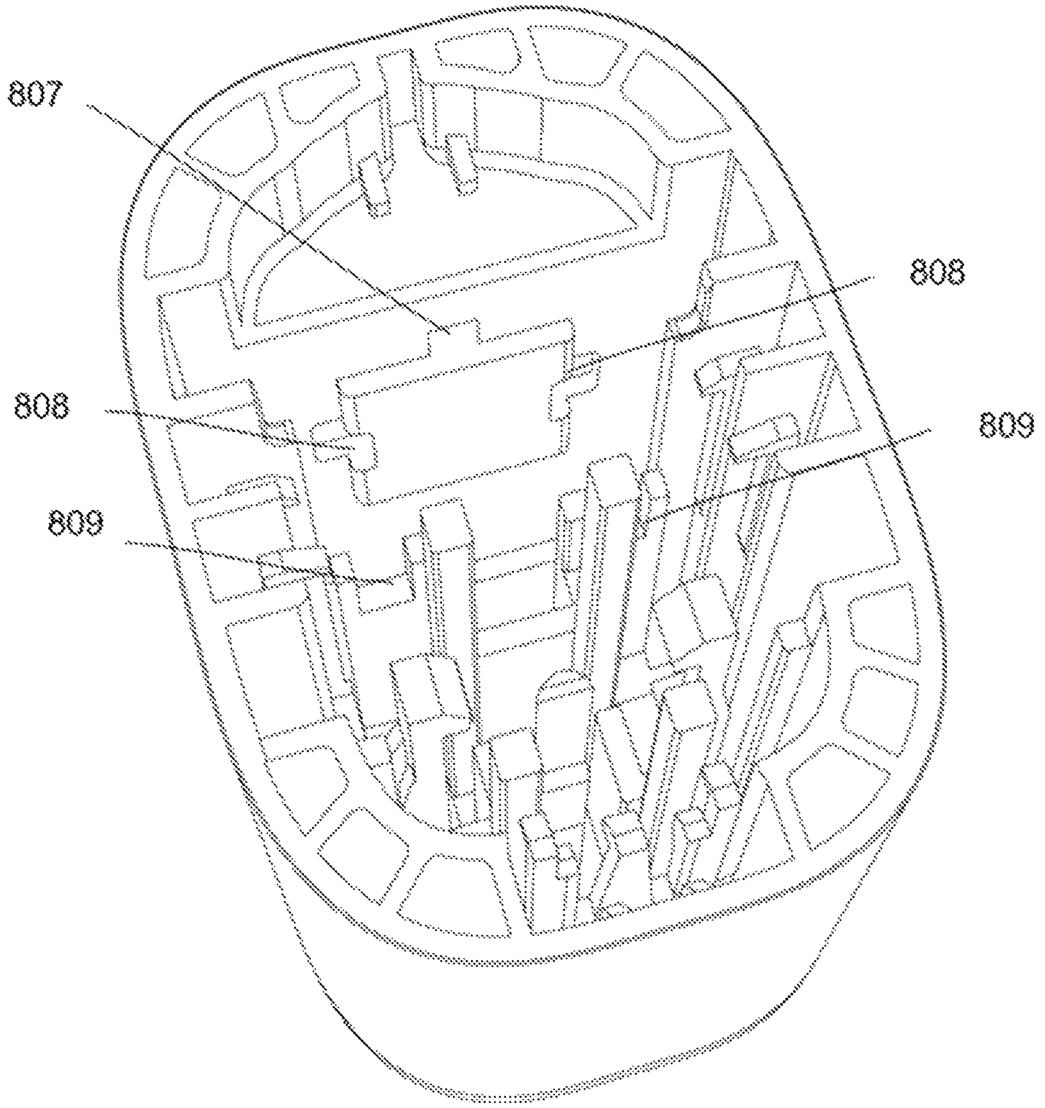
FIG. 2*b* is the schematic diagram of the three-dimensional structure of an exemplary outer shell according to the invention.
Figure 2C:
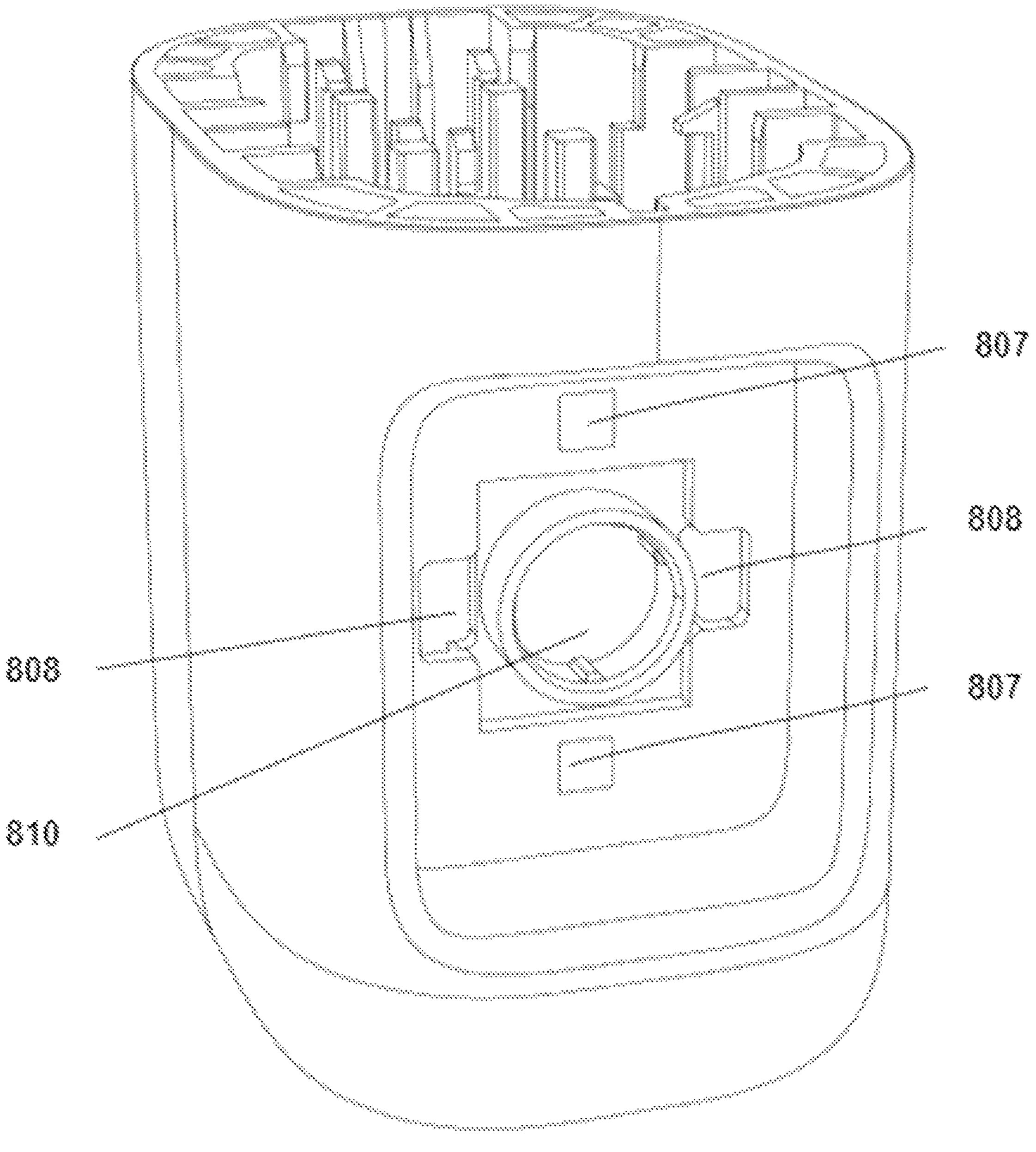
FIG. 2*c* is the schematic diagram of the three-dimensional structure of an exemplary outer shell according to the invention.

FIG. 1*a* is the schematic diagram of the structure explosion of the installation unit 100 in the embodiment of the invention. The base 10 and the outer shell 80 are clamped together. FIG. 1*b* is the schematic diagram of the sectional structure of the installation unit 100 in the embodiment of the invention before installation, and with reference to the direction shown in FIGS. 1*b* and 1*n* combination with FIGS. 2*a*, 2*b* and 2*c*, FIGS. 2*a*, 2*b* and 2*c* are respectively the three-dimensional structure diagrams of the installation unit outer shell 80 in the embodiment of the invention from different perspectives. The base 10, the auxiliary-needle module 20, the parallel slider module 30 and the trigger button module 40 are all set inside or on the side wall of the outer shell 80. The sensor unit 50 is placed on the lower side of the parallel slider module 30. The elastic component 90 comprises the first elastic component 60 and the second elastic component 70. One end of the first elastic component 60 is sleeved outside the cylinder 203 of the auxiliary-needle module 20 and is placed in the first elastic component placement area 806 of the outer shell 80, the other end is located on the upper side of the parallel slider module 30, one end of the second elastic component 70 is placed in the cylinder 203 of the auxiliary-needle module 20, and the other end is located on the upper side of the parallel slider module 30. The first elastic component 60 is parallel to the central axis of the second elastic component 70. Through the shape and spatial layout design of each structural member, the internal space of the outer shell is reasonably used, making the installation unit simple and compact in structure, small in overall size, and convenient for users to operate.

The outer shell 80 comprises a first clamp part 801 of the outer shell, a second clamp part 802 of the outer shell, a third clamp part 803 of the outer shell, a limit column 804, a guide column 805, a first elastic component placement area 806, a limit hole 807, a through-hole 808, and a limit slot 810 for resetting the elastic component. The third clamp part 803 of the outer shell also comprises a limit bulge 8031. Other structural members such as the base 10, the auxiliary-needle module 20, the parallel slider module 30, the trigger button module 40, the sensor unit 50, the first elastic component 60 and the second elastic component 70 can be assembled on the outer shell through the above structure or combination of structures. The specific assembly method will be detailed below.

Figure 3:
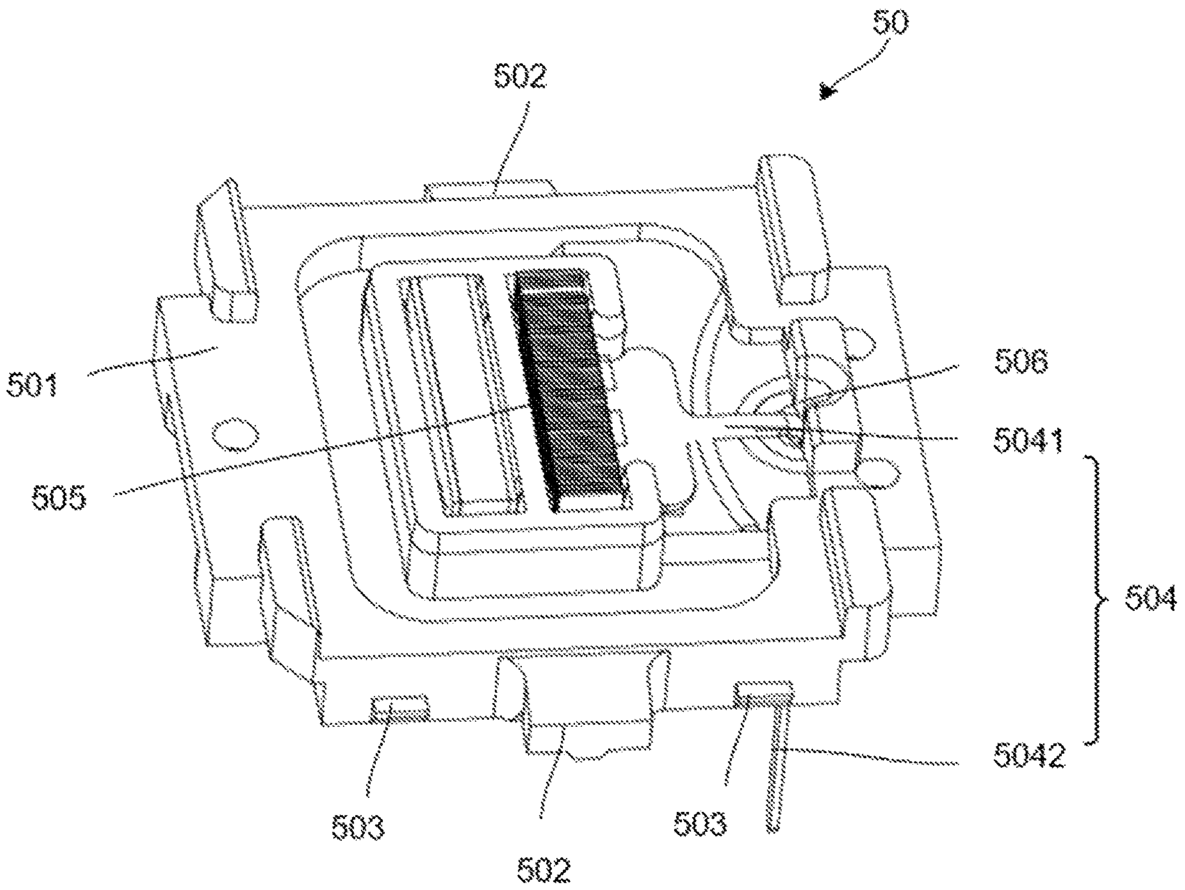
FIG. 3 is the three-dimensional structure diagram of a sensor unit according to an embodiment of the invention.

As shown in FIG. 3 and FIG. 1*b*, the sensor 504 is divided into an external part 5041 and an internal part 5042. The external part 5041 is flat, bent or bent towards the upper surface of the sensor base 501, and laid flat on the upper surface of the sensor base 501, which can reduce the overall thickness of the sensor 504. The internal part 5042 extends to the other side of the sensor base 501 through the puncture hole 506, so as to puncture the subcutaneous. The internal part 5042 and the external part 5041 are perpendicular to each other, so that when the internal part 5042 punctures the subcutaneous, the external part 5041 will not be affected, and the electrode on the sensor 504 will not be broken or damaged, thus improving the detection reliability of the sensor 504.

Figure 6:
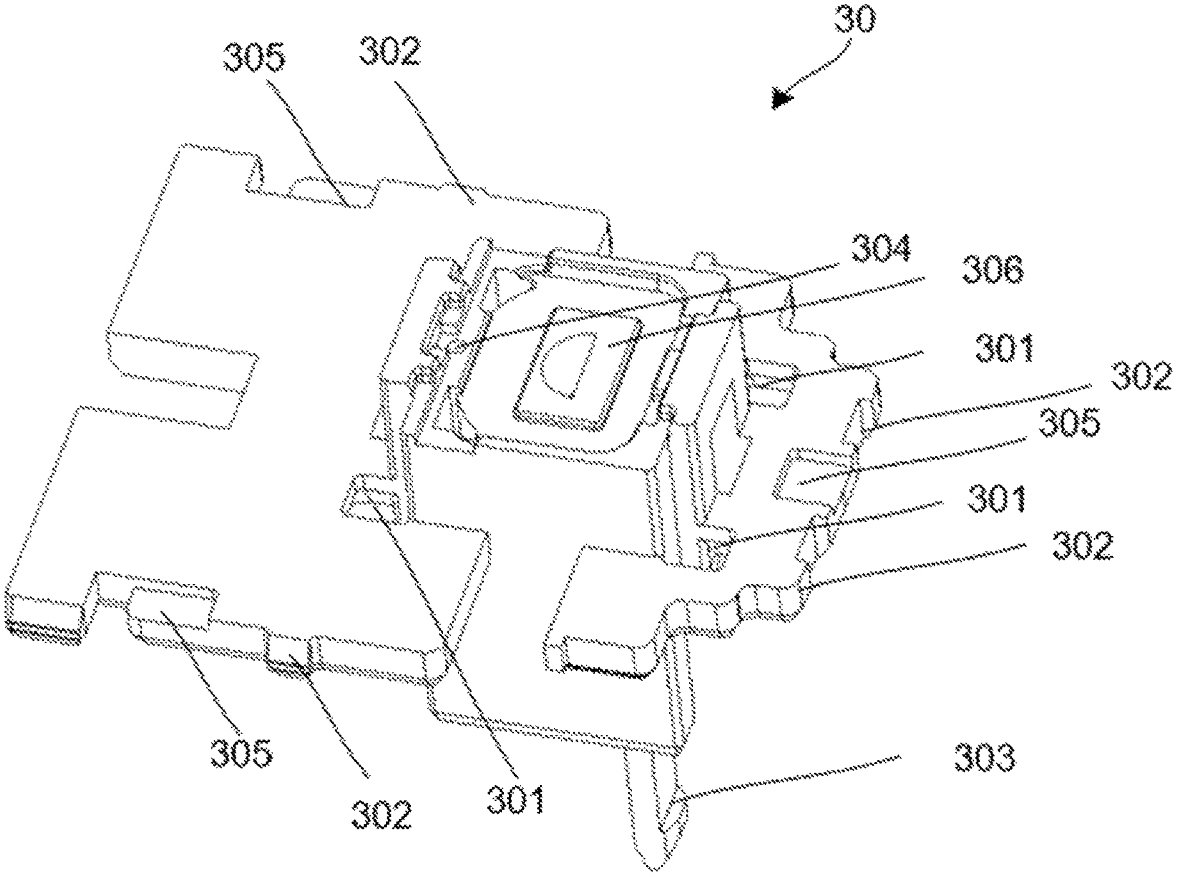
FIG. 6 is the three-dimensional structure diagram of a parallel slider module according to an embodiment of the invention.

With reference to FIG. 6, in the embodiment of the invention, the sensor base 501 of the sensor unit 50 comprises at least two symmetrically arranged sensor first snap portions 502. In the installation unit 100, the sensor unit 50 is placed on the sensor unit placement platform 306 of the parallel slider module 30, and is connected with the first snap portion 801 of the outer shell through the sensor first snap portion 502. The parallel slider module 30 contacts the first elastic component 60, and is connected with the first clamp part 801 of the outer shell through the first clamp part 502 of the sensor unit 50 to resist the elastic force of the first elastic component 60 and keep the first elastic component 60 in a continuous compression state.

In other embodiments of the invention, the first elastic component 60 can be a metal spring or other elastic components, such as elastic rubber, air spring, etc.

Figure 8:
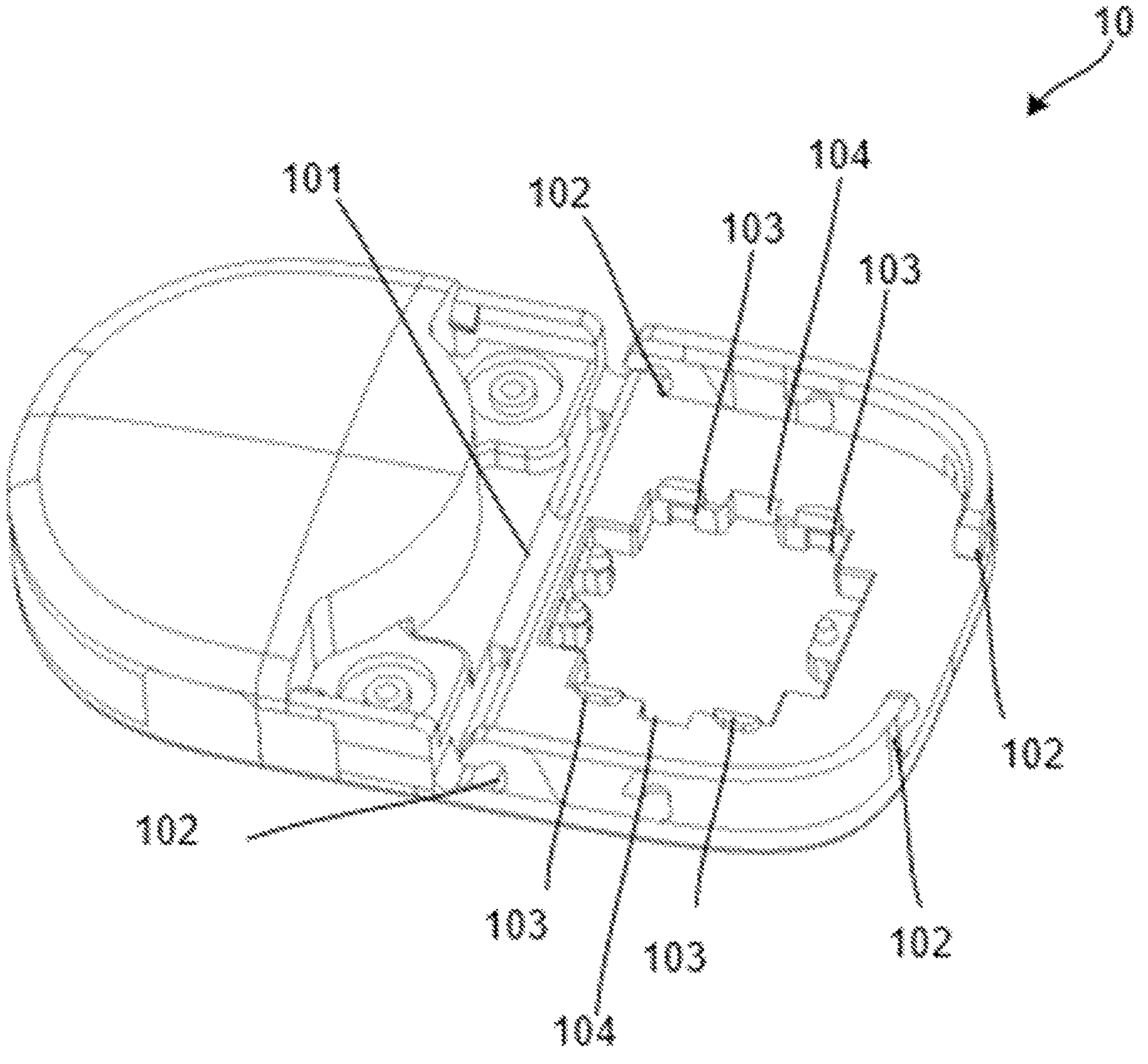
FIG. 8 is the structural diagram of a base according to an embodiment of the invention.

Referring to FIGS. 3 and 8, the sensor base 501 of the sensor unit 50 also comprises at least two symmetrically arranged second sensor engagement portions 503, preferably four, arranged on the same side of the sensor base 501 as the first sensor engagement portion 502. When the sensor unit 50 is installed on the base 10, the second clamp part 503 of the sensor is connected with the second clamp part 103 of the base to fix the sensor unit 50 and the base 10, and the first clamp part 502 of the sensor enters the empty chamber 104.

In the embodiment of the invention, the sensor unit 50 also comprises a circuit unit 505 that contacts the external part 5041. The electrode of the internal part 5042 generates a current signal by detecting the glucose in the human body, which is transmitted to the circuit unit 505 through the external part 5041. The circuit unit 505 then transmits the current signal to the transmitter (not shown in the figure) to prompt the user of glucose related information in the body.

In the embodiment of the invention, the surface of the sensor 504 is provided with an electrode for detecting analyte parameters, an electrode lead and an electric contact (not shown) connected with the electrode lead. Generally, the electrode or electrode lead material is metal or metal compound, such as Ag, Pt, AgCl, etc.

Figure 4A:
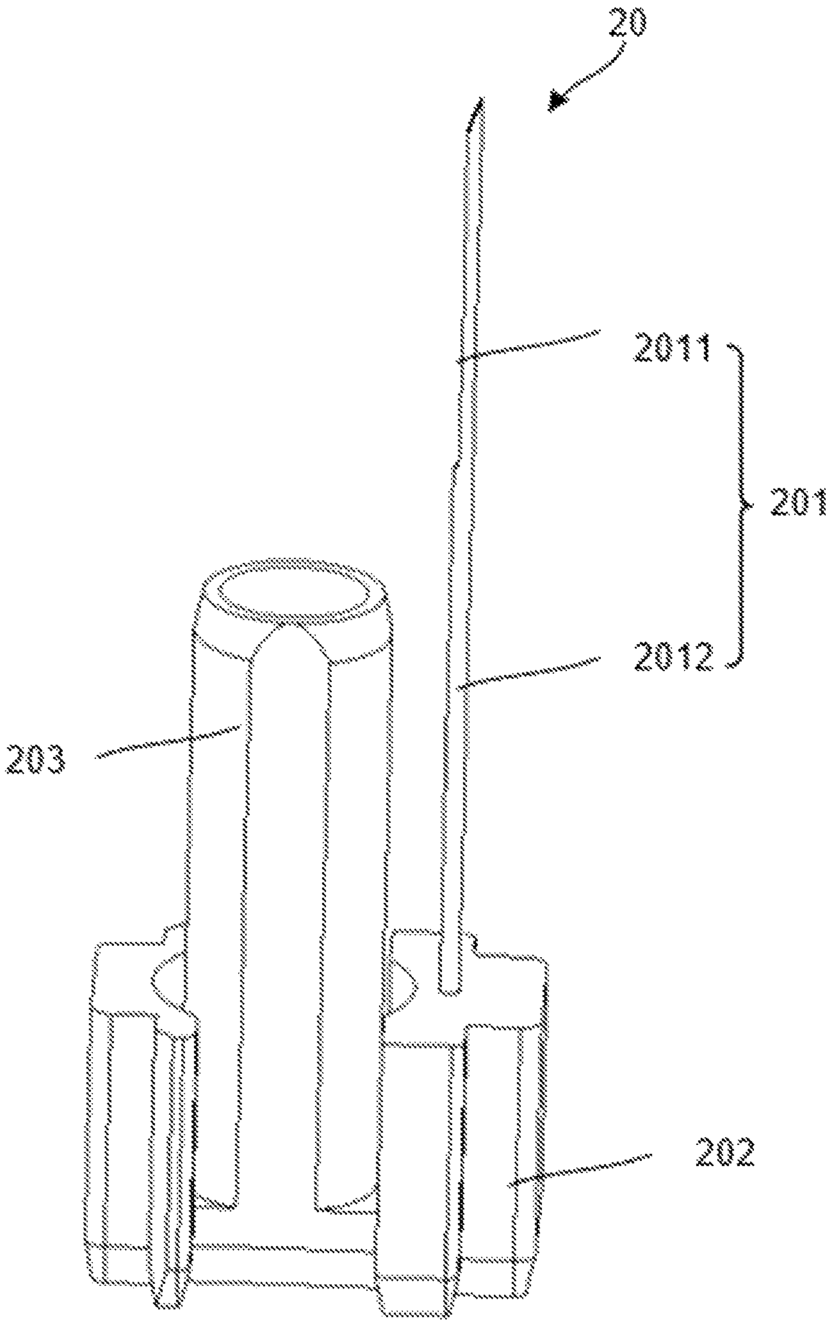
FIG. 4*a* is the schematic diagram of the three-dimensional structure of the auxiliary-needle module according to an embodiment of the invention.

FIG. 4*a* is a three-dimensional schematic diagram of the auxiliary-needle module 20, which is used to help puncture the internal part 5042 under the skin. Generally, the sensor 504 has a certain flexibility. The inner part 5042 of the sensor 504 needs to be carried by the auxiliary-needle 201 to deliver the inner part 5042 into the subcutaneous. The needle body of the auxiliary-needle 201 at least comprises an opening area 2011. The opening area 2011 is arranged at the puncture end of the auxiliary-needle 201. On the one hand, the opening area 2011 can envelop the internal part 5042. When the auxiliary-needle 201 is punctured into the subcutaneous, the internal part 5042 can also enter the subcutaneous. On the other hand, it is convenient to separate the auxiliary-needle 201 from the internal part 5042.

Specifically, in the embodiment of the invention, the sectional shape of the opening area 2011 is circular arc.

In other embodiments of the invention, the section of the opening area 2011 can also be of other shapes, such as "V" shape.

Figure 5:
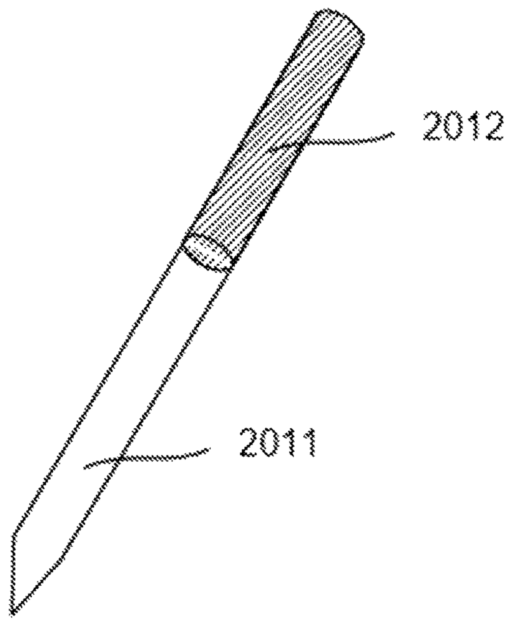
FIG. 5 is the schematic diagram of the three-dimensional structure of an auxiliary-needle according to an embodiment of the invention.

As shown in FIG. 5, in other embodiments of the invention, the needle body of the auxiliary-needle 201 also comprises a closure area 2012, that is, the needle body of the auxiliary-needle 201 is close to the puncture end as an opening area, and the other end is a closure area, which can enhance the bending strength of the auxiliary-needle body.

In other embodiments of the invention, the opening size of the opening area 2011 can be set arbitrarily, and there is no specific restriction here.

In other embodiments of the invention, the body portion 5042 is arranged at the tip portion of the partial opening area 2011. The internal part 5042 can be wrapped by the opening area 2011, or the internal part 5042 only fits with the inner wall of the opening area 2011, and there is no specific restriction here, as long as the internal part 5042 can be sent subcutaneously.

In combination with FIGS. 1*b* and 2*a*, in the embodiment of the invention, the auxiliary-needle module 20 also comprises a chute 202, a limit column 804 that can be embedded in the outer shell, and slides along the limit column 804.

In the embodiment of the invention, the auxiliary-needle module 20 also comprises a cylinder 203, which is parallel to the sliding direction of the auxiliary-needle module 20.

Figure 4B:
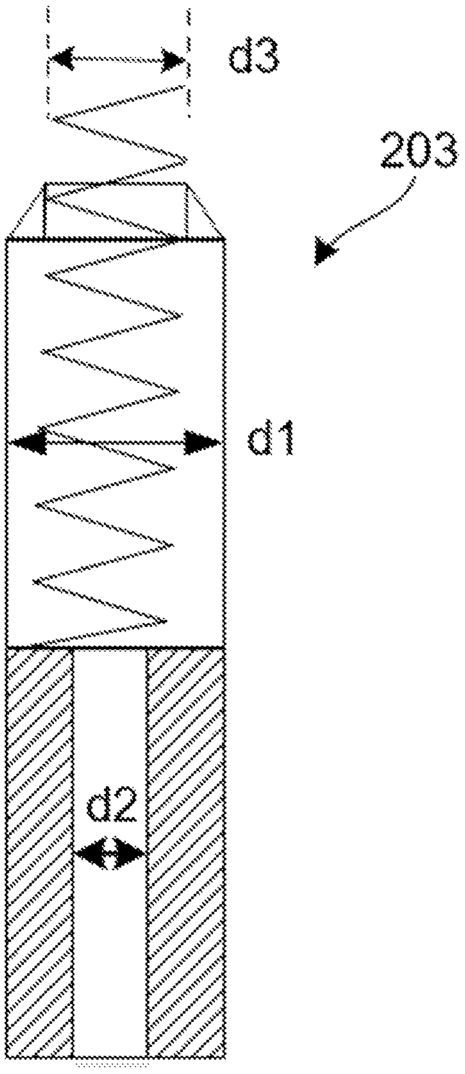
FIG. 4*b* is the sectional structure diagram of the auxiliary-needle module cylinder according to an embodiment of the invention.

In combination with FIG. 4*b*, FIG. 4*b* is the schematic diagram of the sectional structure of the auxiliary-needle module cylinder. The diameter d1 of the side of the inner wall of the cylinder 203 away from the chute 202 is greater than the diameter d2 of the side close to the chute 202. The outer diameter of the second elastic component 70 is d3 and satisfies d1>d3>d2. Therefore, one end of the second elastic component 70 can be placed in the cylinder.

Referring to FIG. 1*b* and FIG. 6, in the embodiment of the invention, the inner side of the cylinder 203 also comprises a cylinder clamp part 2031, which is used to form a clamping connection with the parallel slider clamp part 303 of the parallel slider module 30. The parallel slider clamp part 303 extends into the cylinder, the parallel slider module 30 compresses the second elastic component 70, and the parallel slider clamp part 303 is engaged with the cylinder clamp part 2031, so that the second elastic component 70 is in a continuous compression state.

In the embodiment of the invention, the guide column 805 squeezes the parallel slider clamp part 303 to the cylinder clamp part 2031 to increase the reliability of the clamping connection.

In other embodiments of the invention, the second elastic component 70 can be a metal spring or other elastic components, such as elastic rubber, air spring, etc.

FIG. 6 is the schematic diagram of the three-dimensional structure of the parallel slider module 30. As previously described, the sensor unit placement platform 306 is used to place the sensor unit 50. Combined with FIG. 2*a*, in the embodiment of the invention, the parallel slider module 30 is installed on the limit column 804 of the outer shell 80 through the through-hole 301 of the limit column, so that it can slide along the limit column 804.

In the embodiment of the invention, the auxiliary-needle 201 passes through the auxiliary-needle through-hole 304 of the parallel slider module 30 and the puncture hole 506 of the sensor unit 50 at the same time to ensure that the opening area 2011 of the auxiliary-needle 201 encloses the inner part 5042.

Figure 7:
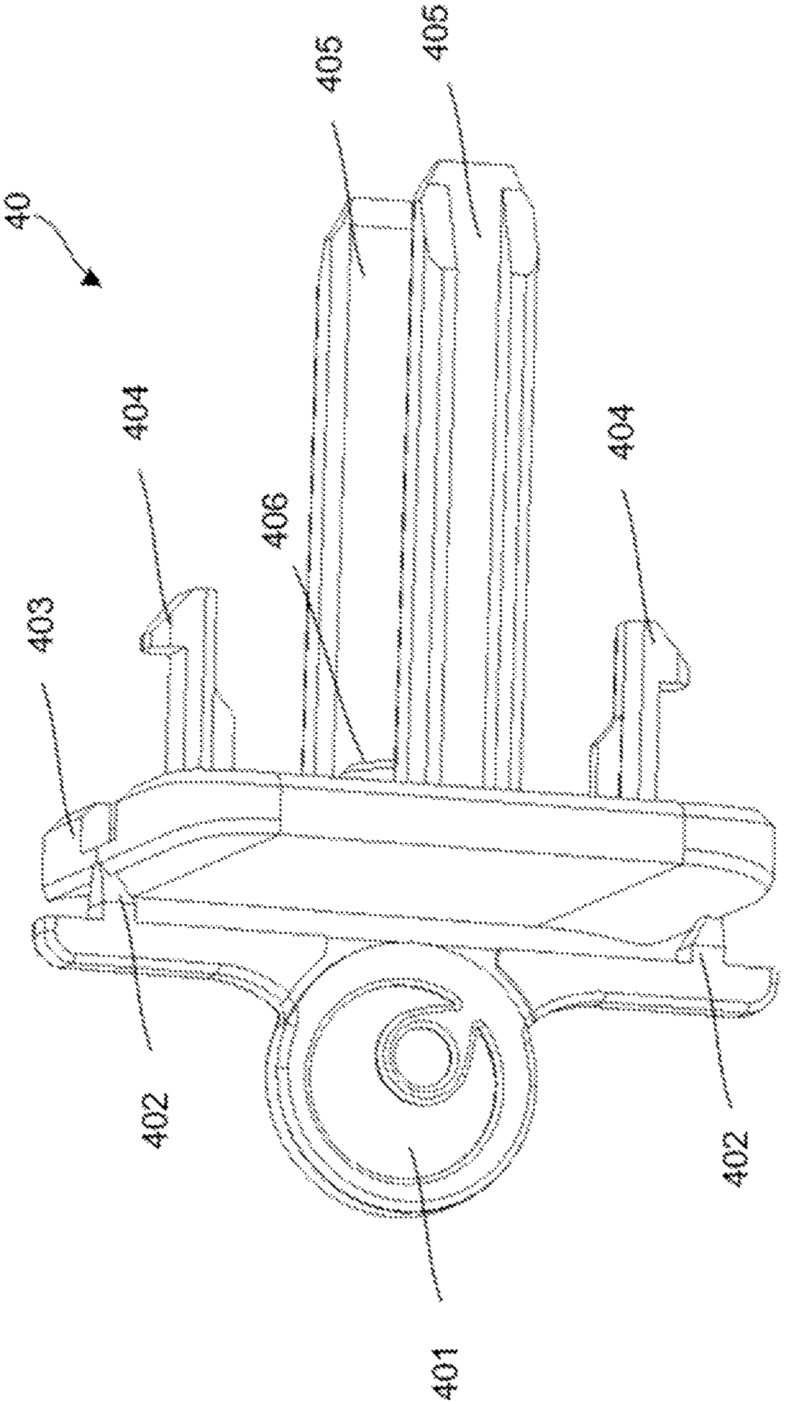
FIG. 7 is the three-dimensional structure diagram of the trigger button module according to an embodiment of the invention.

FIG. 7 is the schematic diagram of the three-dimensional structure of the trigger button module 40. The trigger button module 40 comprises a trigger structure and an anti-trigger structure. The anti-trigger structure is composed of a break button 401 and a breakable structure 402. Before the breakable structure 402 is broken, the break button 401 is pressed against the side wall of the outer shell to prevent the trigger button 403 from moving outward and inside the outer shell.

In combination with FIGS. 1*b* and 2*a*, in the embodiment of the invention, the trigger structure is composed of a trigger button 403 and a trigger paddle 405. After the user breaks the breakable structure 402, the user applies pressure to the trigger button 403, and the trigger button 403 drives the trigger paddle 405 to move towards the inside of the outer shell. The trigger paddle 405 pushes the first clamp part 801 of the outer shell to open it, and cancels the snap connection between the first clamp part 801 of the outer shell and the first clamp part 502 of the sensor, Release the elastic force of the first elastic component 60, and the parallel slider module 30 slides along the limit column 804 under the elastic force of the first elastic component 60, thus starting the triggering action of the installation unit 100.

In combination with FIGS. 2*b* and 2*c*, in the embodiment of the invention, the trigger paddle 405 enters into the outer shell through the through-hole 808 of the outer shell 80, and just contacts the first clamp part 801 of the outer shell before starting the trigger action.

In other embodiments of the invention, the outer shell 80 also comprises a limit groove column 809, and the trigger paddle 405 passes through the groove of the limit groove column 809 to limit the orientation of the trigger paddle 405 in the outer shell 80, ensure that the trigger paddle 405 can accurately contact the first clamp part 801 of the outer shell, and improve the reliability of the installation unit 100 to start the trigger action.

In order to prevent the user from pressing the trigger button 403 and failing to successfully start the trigger action, in other embodiments of the invention, the trigger button module 40 also comprises a reset structure, which can be returned to the initial position after the trigger button 403 is pressed, so that the user can try many times to improve the reliability of the installation unit 100 to start the trigger action. Referring to FIG. 1*b*, the reset structure is composed of reset elastic component 407, limit clip 404 and reset elastic component limit column 406. The limit clip 404 enters the outer shell through the limit hole 807 of the outer shell 80 and forms a snap connection with the inner wall of the outer shell. When the user presses the trigger button 403, the reset elastic component 407 stores the elastic force. After the user releases his hand, the trigger button 403 returns to the initial position under the elastic force of the reset elastic component 407. One end of the reset elastic component 407 is fixed on the reset elastic component limit column 406, and the other end is fixed in the reset elastic component limit slot 810 of the outer shell 80.

In the embodiment of the invention, there is only one trigger button 403, which is located on one side of the outer shell 80. In other embodiments of the invention, there can also be two trigger buttons 403, which are respectively located on the opposite sides of the outer shell 80. The other trigger structures corresponding to the two trigger buttons 403 are consistent. It can be expected that no matter whether there is one or two trigger buttons 403, the user can start the trigger action with one hand to facilitate the user's use.

FIG. 8 shows the three-dimensional structure of the base 10. Before starting the trigger action, the base 10 is connected with the outer shell 80 and forms a closed space with the outer shell.

Referring to FIG. 1*b*, in the embodiment of the invention, the base 10 comprises a housing 101, and the housing 101 comprises a first clamp part 102 of the base, which is used for clamping and connecting with the third clamp part 803 of the outer shell to fix the base 10 on the outer shell.

Referring to FIG. 1*a*, in the embodiment of the invention, the base 10 comprises adhesive tape 105 on the side far from the outer shell 80, which is used to paste the base 10 on the surface of human skin.

In other embodiments of the invention, the base 10 can also be fixed on the outer shell 80 by friction fit.

Continuing to refer to FIG. 1*b*, as described above, after starting the trigger action, the first clamp part 801 of the outer shell and the first clamp part 502 of the sensor release the snap connection, the first elastic part 60 releases the elastic force, and pushes the parallel slider module 30 and the auxiliary-needle module 20 to slide together toward the base 10.

During the sliding process of the parallel slider module 30, the parallel slider protrusion 302 cooperates with the limit bulge 8031, pushes the third clamp part 803 of the outer shell, so as to release the snap connection between the third clamp part 803 of the outer shell and the base clamp part 102, and the base 10 is separated from the outer shell 80.

In the embodiment of the invention, the parallel slider module 30 and the auxiliary-needle module 20 slide together in the direction of the base 10 until the clamping baffle 305 of the parallel slider module 30 is blocked by the second clamp part 802 of the outer shell, and the parallel slider module 30 and the auxiliary-needle module 20 no longer slide in the direction of the base 10.

In the embodiment of the invention, the sensor unit 50 is pushed to the base 10 by the parallel slider module 30, and is clamped to the base 10 through the second clamp part 503 of the sensor and the second clamp part 103 of the base.

In the embodiment of the invention, when the auxiliary-needle module 20 slides in the direction of the base 10, the auxiliary-needle 201 completes the subcutaneous puncture, and the internal part 5042 of the sensor 504 is punctured into the subcutaneous. At the same time, the guide column 805 no longer squeezes the parallel slider engagement portion 303 towards the cylinder engagement portion 2031, the parallel slider engagement portion 303 and the cylinder engagement portion 2031 are released from the engagement connection, the second elastic component 70 releases the elastic force, and the auxiliary-needle module 20 is pushed back to the initial position, which can prevent the auxiliary-needle 201 from being exposed outside the outer shell 80, causing unnecessary safety accidents.

Figure 9:
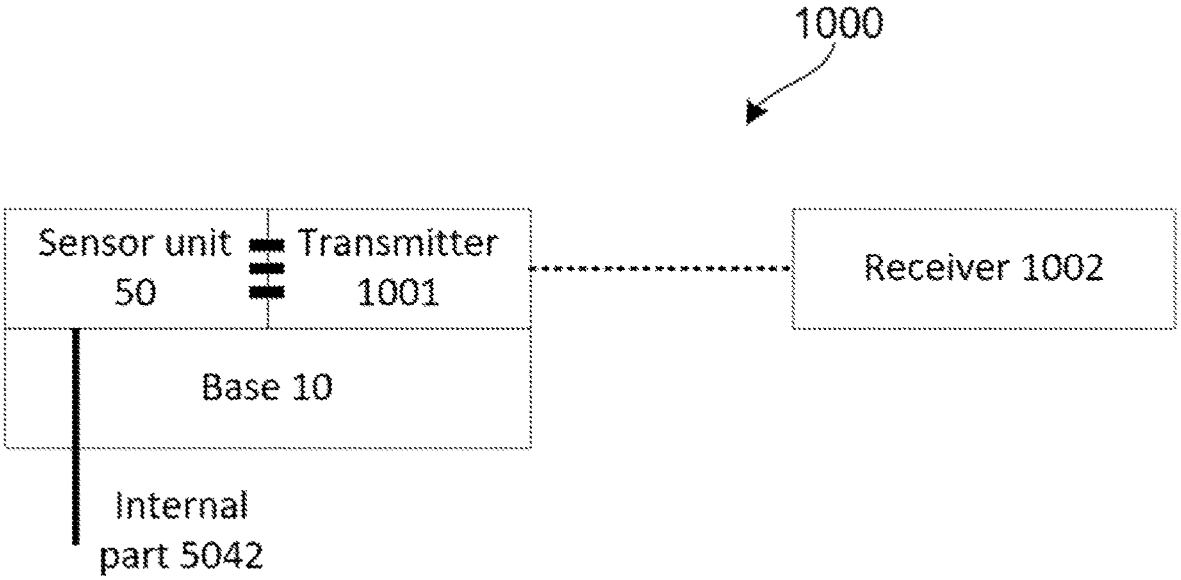
FIG. 9 is the schematic diagram of an analyte detection device according to an embodiment of the invention.

FIG. 9 is the schematic diagram of the analyte detection device 1000. The analyte detection device 1000 comprises a sensor unit 50, a base 10, a transmitter 1001 and a receiver 1002. Before being installed on the human body, the base 10, the sensor unit 50 and the transmitter 1001 are in a separate state. During installation, first paste the base 10 on the surface of human skin with adhesive tape 105, then install the sensor unit 50 on the base 10 through the installation unit 100, and at the same time puncture the internal part 5042 under the skin to complete the installation of the sensor unit 50 base 10 on the surface of human skin.

To sum up, the installation unit of the analyte detection device disclosed by the invention makes the installation unit simple and compact in structure and small in overall size through the shape and spatial layout design of each structural member, thereby reducing the production cost and facilitating the use of users.

Although some specific embodiments of the invention have been detailed through examples, technicians in the field should understand that the above examples are for illustrative purposes only and are not intended to limit the scope of the invention. Persons skilled in the field should understand that the above embodiments may be modified without departing from the scope and spirit of the invention. The scope of the invention is limited by the attached claims.

What is claimed is:

1. An installation unit of analyte detection device, comprising:

a sensor unit, comprising a sensor base and a sensor arranged on the sensor base, and the sensor comprising an external part and an internal part;

a trigger component, wherein an installation unit does not implement an installation action before starting the trigger component;

an auxiliary-needle module, comprising an auxiliary-needle, wherein the auxiliary-needle at least comprises an opening area which encloses the internal part and is suitable for feeding the internal part into a subcutaneous;

a parallel slider module suitable for carrying the sensor unit;

a base embedded into the installation unit from a front end of the installation unit, wherein an installation area suitable for installing the sensor unit is arranged on the base, and the sensor unit is detachably connected to the base;

an outer shell used for carrying the trigger component, the auxiliary-needle module, the parallel slider module and the base;

an elastic component, sleeved on the auxiliary needle module, wherein the elastic component comprises the first elastic component and the second elastic component, in a compressed state and suitable for providing the elastic force required by the installation unit to implement the installation action, when the auxiliary-needle module and the parallel slider module slide in a direction toward the base, the sensor unit is clamped to the base, and the auxiliary-needle completes a subcutaneous puncture.

2. The installation unit of analyte detection device of claim 1, wherein the external part is a plane structure.

3. The installation unit of analyte detection device of claim 2, wherein the external part is bent or bent towards a top of the sensor base, laid flat on the top of the sensor base, and the external part is in a working position.

4. The installation unit of analyte detection device of claim 3, wherein the external part and the internal part are perpendicular.

5. The installation unit of analyte detection device of claim 1, wherein the outer shell is provided with a first clamp part on the outer shell, the sensor unit is provided with a first clamp part of the sensor, and the first clamp part of the outer shell and the first clamp part of the sensor are mutually clamped.

6. The installation unit of analyte detection device of claim 5, wherein the trigger component comprises a trigger paddle, the outer shell comprises a through-hole arranged on a side wall, and the trigger paddle enters into the outer shell through the through-hole.

7. The installation unit of analyte detection device of claim 6, wherein when implementing the installation action, the trigger paddle pushes the first clamp part of the outer shell to release a snap state of the first clamp part of the outer shell and the first clamp part of the sensor.

8. The installation unit of analyte detection device of claim 1, wherein the trigger component comprises a trigger button and an anti-trigger structure, the anti-trigger structure comprises a breakable structure and a break button, and the break button is suitable for preventing the trigger button from starting before a break of the breakable structure, thereby implementing the installation action.

9. The installation unit of analyte detection device of claim 1, wherein the trigger component comprises a reset elastic component, which is suitable for returning the trigger button to an initial position after starting.

10. The installation unit of analyte detection device of claim 9, wherein the trigger component also comprises a limit clip, the outer shell comprises a limit hole, and the limit clip and the limit hole form a snap connection to prevent the trigger button from separating from the outer shell when the trigger button returns to the initial position.

11. The installation unit of analyte detection device of claim 1, wherein the opening area is circular arc or "V" shape.

12. The installation unit of analyte detection device of claim 1, wherein the outer shell comprises a limit column, the auxiliary-needle module comprises a chute, the parallel slider module comprises a through-hole of the limit column, the chute and the through-hole of the limit column are respectively matched with the limit column, which is suitable for making the auxiliary-needle module and the parallel slider module slide in the outer shell.

13. The installation unit of analyte detection device of claim 12, wherein the outer shell is provided with a third clamp part of the outer shell, the base is provided with a first clamp part of the base, and the third clamp part of the outer shell and the first clamp part of the base are mutually clamped, which is suitable for fixing the base on the outer shell.

14. The installation unit of analyte detection device of claim 13, wherein the third clamp part of the outer shell is provided with a limit bulge, and the parallel slider module is provided with a parallel slider bulge, when the parallel slider module slides toward the base direction, the limit bulge and the parallel slider bulge cooperate to push the third clamp part of the outer shell apart, so as to release a snap state of the third clamp part of the outer shell and the first clamp part of the base, and release the base.

15. The installation unit of analyte detection device of claim 1, wherein the first elastic component is located between the outer shell and the parallel slider module.

16. The installation unit of analyte detection device of claim 1, wherein the second elastic component is located between the auxiliary-needle module and the parallel slider module.

17. The installation unit of analyte detection device of claim 16, wherein the auxiliary-needle module is provided with a cylinder clamp part, the parallel slider module is provided with a parallel slider clamp part and a clamping baffle, the outer shell is provided with a second clamp part, the cylinder clamp part and the parallel slider clamp part are mutually clamped, which is suitable for making the auxiliary-needle module slide with the parallel slider module toward a base direction, and when the auxiliary-needle module slides to a position, the clamping baffle is blocked by the second clamp part of the outer shell, the cylinder clamp part and the parallel slider clamp part release elasticity of the second elastic part, the auxiliary-needle module is pushed back to the initial position.

18. The installation unit of analyte detection device of claim 1, wherein the installation area of the base is provided with a second clamp part of the base, the sensor unit is provided with a second clamp part of the sensor, when the sensor unit is assembled to the base, the second clamp part of the base forms a snap connection with the second clamp part of the sensor.

19. The installation unit of analyte detection device of claim 1, wherein the base comprises an adhesive tape, which is suitable for pasting the base on a surface of human skin.

* * * * *